US006254635B1

(12) United States Patent
Schroeder et al.

(10) Patent No.: US 6,254,635 B1
(45) Date of Patent: *Jul. 3, 2001

(54) CALCIFICATION-RESISTANT MEDICAL ARTICLES

(75) Inventors: Richard F. Schroeder, Oakdale; Matthew F. Ogle, St. Paul, both of MN (US)

(73) Assignee: St. Jude Medical, Inc., St. Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/017,185

(22) Filed: Feb. 2, 1998

(51) Int. Cl.[7] .................................................... A61F 2/24

(52) U.S. Cl. ........................................ 623/2.13; 623/23.72

(58) Field of Search .............................. 623/2, 3, 11, 16, 623/66, 2.1, 2.12, 2.13, 2.42, 23.72, 23.73; 427/2.1, 2.24

(56) References Cited

U.S. PATENT DOCUMENTS

| 4,167,045 | 9/1979 | Sawyer ....................................... 3/1.4 |
| 4,378,224 | 3/1983 | Nimni et al. ........................... 8/94.11 |
| 4,648,881 | * 3/1987 | Carpentier et al. ....................... 623/2 |
| 4,753,652 | 6/1988 | Langer et al. ............................. 427/1 |
| 4,770,665 | 9/1988 | Nashef et al. .......................... 8/94.11 |
| 4,798,611 | 1/1989 | Freeman .................................. 623/66 |
| 5,094,661 | 3/1992 | Levy ....................................... 8/94.11 |
| 5,104,405 | 4/1992 | Nimni et al. ............................... 623/2 |
| 5,133,956 | 7/1992 | Garlich ................................... 424/1.1 |
| 5,188,834 | * 2/1993 | Grimm et al. .......................... 623/11 |
| 5,215,541 | 6/1993 | Nashef et al. .......................... 8/94.11 |
| 5,368,608 | 11/1994 | Levy ....................................... 8/94.11 |
| 5,464,438 | 11/1995 | Menaker .................................... 623/1 |
| 5,468,562 | 11/1995 | Farivar et al. ......................... 428/457 |
| 5,474,797 | 12/1995 | Sioshansi et al. .................... 427/2.24 |
| 5,520,664 | 5/1996 | Bricault et al. ....................... 604/265 |
| 5,632,778 | * 5/1997 | Goldstein ................................ 623/66 |
| 5,681,575 | 10/1997 | Burrell .................................. 424/423 |
| 5,697,972 | * 12/1997 | Kim et al. ................................. 623/2 |
| 5,728,420 | * 3/1998 | Keogh .................................. 427/2.12 |
| 5,733,339 | * 3/1998 | Girardot et al. .......................... 623/2 |
| 5,882,850 | * 3/1999 | Khor et al. ............................... 623/2 |

FOREIGN PATENT DOCUMENTS

| 0 121 008 | 10/1989 | (EP) . |
| WO 88/01155 | 2/1988 | (WO) . |
| WO 94/01481 | 1/1994 | (WO) . |
| WO 95/11047 | 4/1995 | (WO) . |

OTHER PUBLICATIONS

Aminodiphosphonate or AL +++ Preincubation Inhibits Calicification of Aortic Homografts in the Rat Subdermal Model; by Catherine L. Webb et al; ASAIO Transactions; 34 (1988) Jul./Sep., pp. 851–854.

Long–Term Efficacy of $Al^{3+}$ for Prevention of Bioprosthetic Heart Valve Calcification; by Catherine L. Webb et al.; ASAIO Transactions; 36(1990) Jul./Sep., pp. M408–M410.

Synthesis of inorganic nanophase materials in supramolecular protein cages; by Fiona C. Meldrum et al.; Nature; 349 (1991) pp. 684–686.

(List continued on next page.)

Primary Examiner—Michael Milano
(74) Attorney, Agent, or Firm—Peter S. Dardi; Westman, Champlin & Kelly

(57) ABSTRACT

Medical articles can include biocompatible material with a deposit of anticalcific elemental metal. The biocompatible material can be tissue, fabric or the like. The biocompatible material can be configured on the medical article such that when the medical article is positioned for its intended use, the biocompatible material is substantially removed from blood flow or is in a low blood flow area effectively removed from vascular blood flow. Gas phase or solution phase methods can be used to deposit the anticalcific elemental metal.

20 Claims, 5 Drawing Sheets

OTHER PUBLICATIONS

Inhibilitation of Alkaline Phosphatase by Beryllium and Aluminum; by Carlos E. Bamberger et al.; Archives of Biochemistry and Biophysics 123 (1968); pp. 195–200.

Levy et al. Initiation of Mineialization in Bioprosthetic Heart Valves; Studies of Alkaline Phosphatuse activity and its Inhibition by A/c3 or FEC/3 Preinculbations J. Bio–M-eter. Res. 25 (1991) pp. 905–935.

Ferritin: an iron storage protein with diverse functions; by J.G. Joshi et al; Biofactors; 1 (1998); pp. 207–212.

The Hydrolytic Polymerization of Ferric Citrate. I. The Chemistry of the Polymer; by Thomas G. Spiro et al.; J. Amer. Chem. Soc. 89(1967); pp. 556–559.

Prevention of Calcification of Bioprosthetic Heart Valve Leaflets by $Ca^{2+}$ Diphosphonate Pretreatment; by Thomas P. Johnston et al.; J. Pharmaceutical Sci 77 (1988) Sep.; pp. 740–744.

Synergism of calcium–ethanehydroxybisphosphonate (CaE-HBP) abd $FeCl_3$: controlled release polymers for preventing calcification of bioprosthetic aortic wall; by narendra R. Vyavahare et al.; J. Controlled Release 34 (1995) pp. 97–108.

* cited by examiner

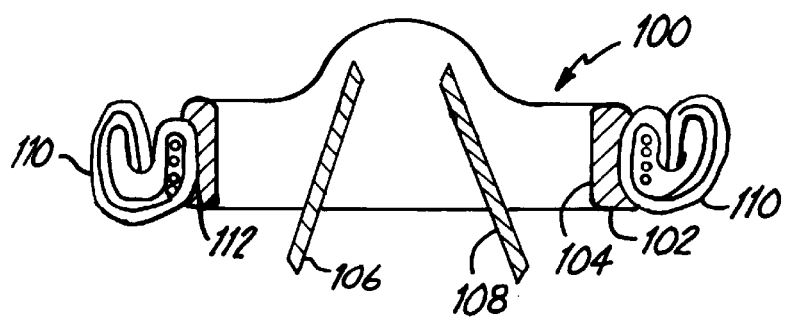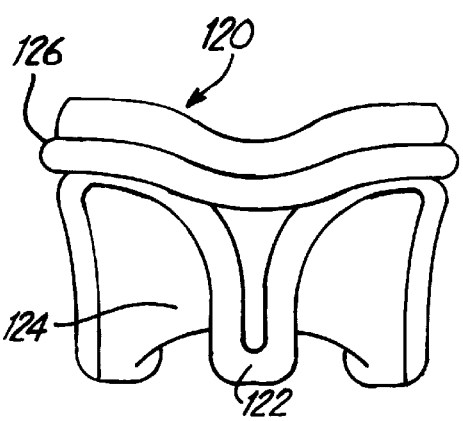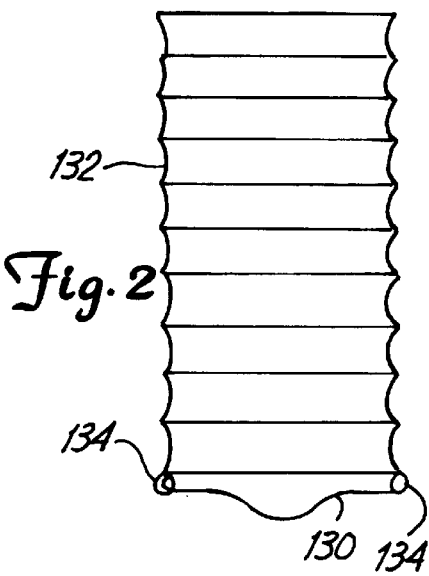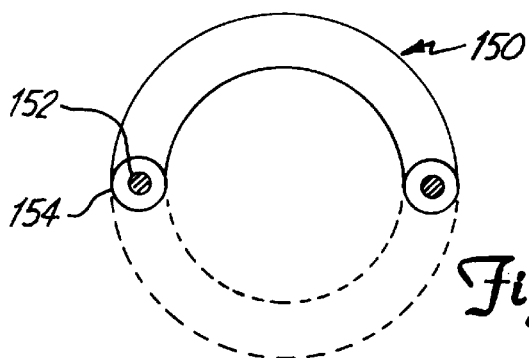

A  B

CALCIFICATION-RESISTANT MEDICAL ARTICLES

FIELD OF THE INVENTION

The invention relates to medical articles having at least a portion designed to contact a patient's bodily fluids and/or tissues, where the medical articles are constructed from biocompatible material that resists calcification. The invention further relates to methods of producing these medical articles.

BACKGROUND OF THE INVENTION

Various medical articles have been designed particularly for contact with a patient's bodily fluids. This contact can be sufficiently long such that calcification of the medical article becomes a concern. Relevant medical articles include, for example, catheters and prostheses. Catheters include percutaneous devices that penetrate the skin to provide access to a bodily system.

Prostheses, i.e., prosthetic devices, are used to repair or replace damaged or diseased organs, tissues and other structures in humans and animals. Prostheses must be generally biocompatible since they are typically implanted for extended periods of time. Specifically, prostheses include artificial hearts, artificial heart valves, annuloplasty rings, ligament repair material, vessel repair structures, surgical patches constructed of mammalian tissue and the like. Prostheses can be constructed from natural materials, synthetic materials or a combination thereof.

Calcification, i.e., the deposit of calcium salts especially calcium phosphate (hydroxyapatite), can occur in and on some materials of a medical article while contacting the patient's bodily fluids. Calcification can affect the performance and structural integrity of medical articles constructed from these calcification sensitive materials, especially over extended periods of time. For example, calcification is the primary cause of clinical failure of bioprosthetic heart valves made from porcine aortic valves or bovine pericardium. Calcification is particularly severe at stress points where suture passes through tissue. Calcification also significantly affects the performance of prostheses constructed from synthetic materials, such as polyurethane.

The importance of bioprosthetic animal heart valves as replacements for damaged human heart valves has resulted in a considerable amount of interest in the effects of calcification on these xenotransplants. Bioprosthetic heart valves from natural materials were introduced in the early 1960's. Bioprosthetic heart valves typically are derived from pig aortic valves or are manufactured from other biological materials such as bovine pericardium. Xenograft heart valves are typically fixed with glutaraldehyde prior to implantation to reduce the possibility of immunological rejection. Glutaraldehyde reacts to form covalent bonds with free amino groups in proteins, thereby chemically crosslinking nearby proteins.

Generally, bioprosthetic heart valves begin failing after about seven years following implantation, and few bioprosthetic valves remain functional after 20 years. Replacement of a degenerating valve prosthesis subjects the patient to additional surgical risk, especially in the elderly and in situations of emergency replacement. While failure of bioprostheses is a problem for patients of all ages, it is particularly pronounced in younger patients. Over fifty percent of bioprosthetic valve replacements in patients under the age of 15 fail in less than five years because of calcification.

Similarly, calcification of polyurethane bladders in artificial hearts and of leaflets in polyurethane valves is potentially clinically significant. Other prostheses made from natural and/or synthetic materials also display clinically significant calcification.

As a result, there is considerable interest in preventing the deposit of calcium on implanted biomaterials, especially heart valves. Research on the prevention of calcification has focused to a considerable extent on the pretreatment of the biomaterial prior to implantation. Detergents (e.g., sodium dodecyl sulfate), toluidine blue or diphosphonates have been used to pretreat tissues in an attempt to decrease calcification by reducing calcium nucleation. Within a relatively short time, these materials tend to wash out of the bioprosthetic material into the bodily fluids surrounding the implant, limiting their effectiveness.

Other approaches to reducing calcification have employed a chemical process in which at least some of the reactive glutaraldehyde moieties are inactivated. Still other approaches have included development of alternative fixation techniques, since evidence suggests that the fixation process itself contributes to calcification and the corresponding mechanical deterioration. In addition, since nonviable cells present in transplanted tissue are sites for calcium deposition, various processes have been developed to remove cellular material from the collagen—elastin matrix of the tissue prior to implantation.

A significant advance toward reducing calcification of bioprostheses was the determination that $Al^{+3}$ cations and other multivalent cations inhibit calcification. Biocompatible materials were treated with an acidic, aqueous solution of $AlCl_3$ prior to implantation. While some of the $Al^{+3}$ cations wash away after being removed from the treatment solution, a significant quantity of cations remain joined with the treated materials for extended periods, presumably due to some type of association of the cations with the bioprosthetic material.

The associated $Al^{+3}$ cations are found to contribute to significant inhibition of calcium deposition. Furthermore, this effect persists over a significant period, at least several months in a juvenile animal. Treatment with $Fe^{+3}$ salts is observed to produce similar reductions in calcification.

Physiologically normal calcification of skeletal and dental tissues and pathological calcification, such as calcification of bioprostheses, have important similarities including the initial deposit of apatitic mineral. These mineral deposits contain calcium and phosphates, and mineral growth takes place at nuclei provided by initial deposits. Nucleation in bone development takes place at structures that have a high concentration of calcium binding phospholipids and high activity of phosphatases, especially alkaline phosphatase. Alkaline phosphatase activity is particularly high in children, which may contribute to the severe calcification problem for bioprostheses implanted into young patients.

Phosphatase activity is found to be inhibited by incubation with $AlCl_3$ and $FeCl_3$. This observation suggests that the effect of $Al^{+3}$ and $Fe^{+3}$ cations in reducing calcification may be due to the inhibition of the phosphatase activity. Alternatively or in addition, the ions may act by substitution into the hydroxyapatite crystal lattice which could prevent growth by destabilizing the crystal.

SUMMARY OF THE INVENTION

Medical articles can include one or more portions of biocompatible material with deposits of anticalcific elemental metal. The anticalcific elemental metal provides a source of anticalcific metal ions upon oxidation of the metal. Reduction of calcification can result in less deterioration of the article with a corresponding prolonged period of effective function. Use of an anticalcific elemental metal can result in the gradual and relatively long term release of anticalcific metal ions. A variety of methods can be used to deposit the anticalcific elemental metal. Anticalcific elemental metal can be combined with other anticalcific agents to obtain further reductions in calcification.

Approaches based on anticalcific elemental metal can deliver effective quantities of anticalcific elemental metal ions to tissue without damaging the tissue. The approach can be used to deliver the ions to portions of tissue particularly sensitive to calcification, for example, by attaching metal coated fabric near the sensitive portion of the tissue. The release rate can be adjusted by changing conditions to accelerate or decelerate the corrosion of the anticalcific metal.

In a first aspect, the invention features a medical article including a biocompatible material, the biocompatible material including anticalcific elemental metal. The biocompatible material is suitable for contact with a patient's internal bodily fluids and tissues. Preferably, the biocompatible material is positioned within the medical article such that the biocompatible material is in a low blood flow area when the medical article is used for its intended purpose. The anticalcific elemental metal can include a metal such as aluminum, iron, magnesium or combinations thereof. The biocompatible material can include greater than about 0.01 mg of the elemental metal per gram of dry biocompatible material.

In certain embodiments, the biocompatible material includes a fabric where the fabric has a deposit of the anticalcific elemental metal. The medical article can include a heart valve prosthesis where the heart valve prosthesis has an orifice (orifice ring) with an interior and an exterior. The orifice forms a passage for the flow of blood with the blood flow contacting the interior of the orifice. The fabric forming a sewing cuff is secured to the exterior of the orifice. The calcification of the medical article preferably is reduced at least about 30 percent following about one month of implantation within a patient, the reduction being determined in comparison with a comparable medical article lacking the elemental metal. The medical article further can include a deposit of an anticalcific metal compound. In certain embodiments, the medical article comprises a heart valve prosthesis, the heart valve prosthesis including tissue forming an annulus with the interior of the annulus defining a blood flow path, and wherein the biocompatible material comprises fabric located on the outside of the annulus.

In another aspect, the invention features a method including distributing a medical article as described above for use under the supervision of a health care professional.

In another aspect, the invention features a medical article including tissue, the tissue including a deposit of anticalcific, elemental metal. The medical article can be a heart valve prosthesis. The tissue can include crosslinked and/or uncrosslinked tissue. The tissue preferably includes a deposit of at least about 0.01 mg of elemental metal per gram of tissue.

In another aspect, the invention features a method of producing a medical article including a biocompatible material, the method including depositing anticalcific elemental metal on at least a portion of a substrate to form the biocompatible material. In these embodiments, the deposition is performed with the biocompatible material contacting a solution comprising oxidized forms of the anticalcific metal. The deposition step can include chemical reduction to deposit elemental metal from the solution. The deposition can include electroplating. The substrate can include fabric and/or tissue. The method further can include attaching fabric to additional components to form the medical article.

In another aspect, the invention features a method of producing a medical article including a biocompatible material, the method including depositing anticalcific elemental metal on at least a portion of a substrate to form the biocompatible material. The biocompatible material is suitable for contact with a patient's internal bodily fluids and tissues and can be located on the medical article such that the biocompatible material is removed substantially from any blood flow when the medical article is used for its intended purpose. The biocompatible material can be a sewing cuff including fabric, and the deposition step can include vapor deposition.

In another aspect, the invention features a medical article including a biocompatible material, the biocompatible material including elemental metal such as iron, magnesium, zinc, gallium, lanthanum or beryllium. The biocompatible material can be suitable for contact with a patient's internal bodily fluids and tissues. The biocompatible material can be removed substantially from any blood flow when the medical article is used for its intended purpose.

In another aspect, the invention features suture including a thread in an unwoven configuration coated with an anticalcific elemental metal.

Other features and advantages of the invention are apparent from the following detailed description of the invention and the claims.

BRIEF DESCRIPTION OF THE DRAWINGS

FIG. 1A is a sectional view of a mechanical heart valve prosthesis taken through the center of the sewing cuff.

FIG. 1B is a side view of a heart valve prosthesis with polymer leaflets.

FIG. 2 is a side view of the mechanical heart valve prosthesis of FIG. 1 with an attached aortic graft.

FIG. 3 is a perspective sectional view of an annuloplasty ring prosthesis with the cut away portions of the ring indicated with dashed lines.

DESCRIPTION OF THE PREFERRED EMBODIMENTS

Figure 4:
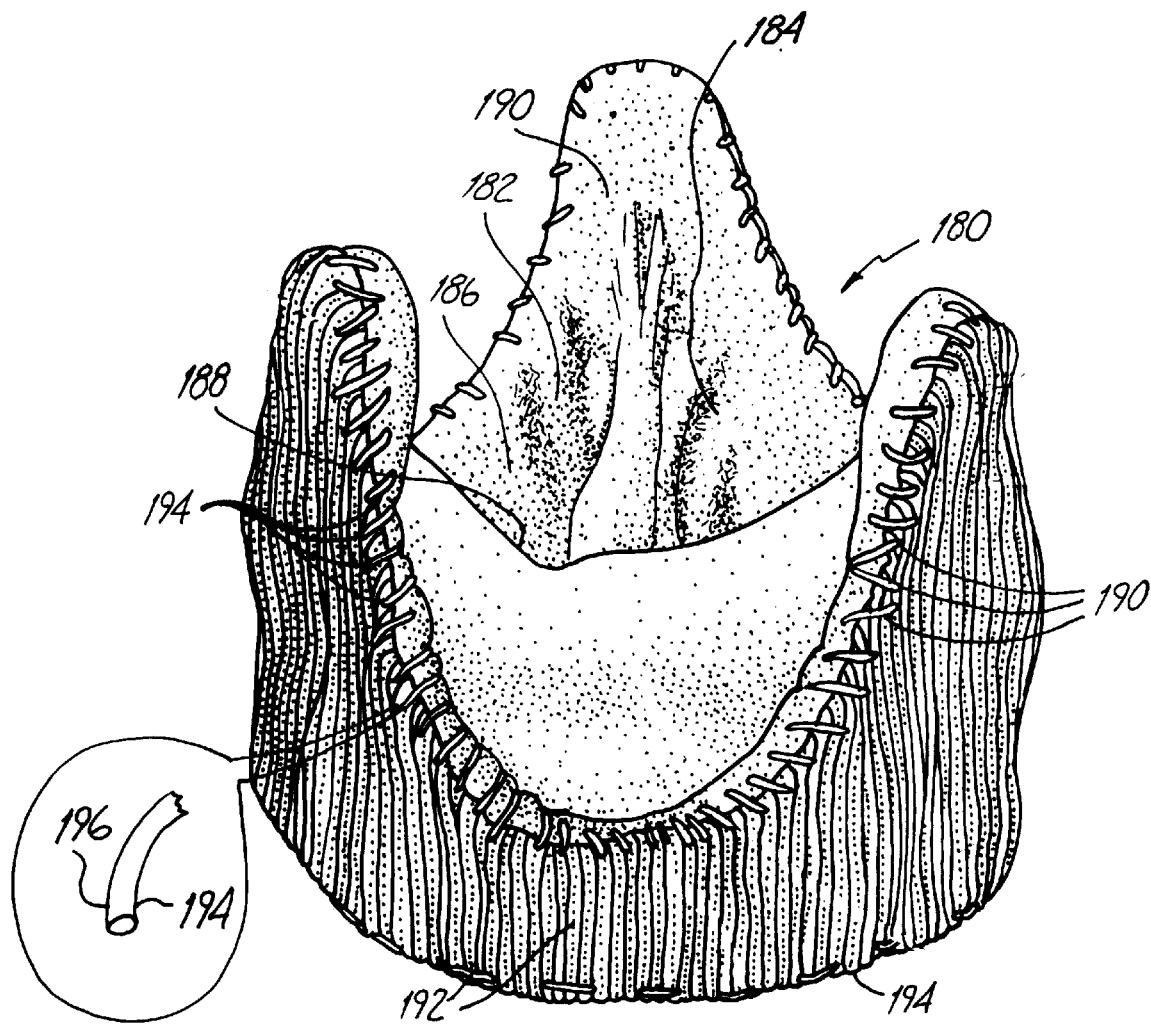
FIG. 4 is a perspective view of a tissue heart valve prosthesis.

To impart a medical article with resistance to calcification, the medical article can be supplied with a deposit of elemental metal that gradually forms metal ions upon oxidation. Deposits of anticalcific elemental metal can provide a long lasting source of metal ions that inhibit calcification. The quantity and type of metal deposits can be selected to provide a desired degree of calcification inhibition. The deposition of anticalcific elemental metal can be combined with other approaches to provide further improved calcification inhibition.

A variety of medical articles can be used to contact bodily fluids of a patient. Relevant medical articles generally incorporate a biocompatible material that is intended to contact the patient's biological fluids and/or tissues. Bodily fluids include, for example, blood, plasma, serum, interstitial fluids, saliva and urine. The patient can be an animal, especially a mammal, and preferably is a human.

Any degree of inhibition of calcium deposition is useful, given the association between calcification and deterioration of prostheses. A preferred degree of inhibition results in a reduction of calcium deposition by at least about 30 percent, preferably at least about 50 percent and more preferably at least about 75 percent after about a one month period in contact with a patient's bodily fluids and/or tissues, when compared with a comparable medical article without deposits of anticalcific elemental metal. The deposit of elemental metal should not inhibit the mechanical functioning of the medical device or provide a toxic level of metal ions within the patient's fluids given the rates of dissolution and the excretion of the metal by the patient. Association of anticalcific metal with suture should reduce the severe calcification associated with passing suture through tissue.

In certain embodiments, biocompatible material with deposits of anticalcific elemental metal is located on the medical article such that this biocompatible material is removed substantially from blood flow when the medical article is used for its intended purpose. In other words, when the medical article is in position for use in contact with a patient's bodily fluids or tissues, biocompatible material associated with the medical article does not contact any blood flow except possibly for a small portion of the biocompatible material such as an edge of the material at a seam. In other embodiments, the biocompatible material with anticalcific elemental metal can be located completely in a low blood flow area where the biocompatible material experiences effectively no vascular blood flow. Such medical articles can include additional portions of biocompatible material with deposits of anticalcific elemental metal.

Various methods can be employed for associating elemental metal with the biocompatible material of a medical article. Vapor phase methods basically involve the accumulation of metal onto the surface of the biocompatible material from a gas phase. Other methods involve the reaction of metal solutions with a chemical reductant. In addition, elemental metal can be deposited by electrochemical reduction.

Particular methods may be more suitable for the deposition of metal into and/or onto certain types of biocompatible material. Using the various methods described below, a large variety of materials can be produced with associated anticalcific elemental metal. In preferred embodiments, elemental metal is directed specifically to or near portions of a medical article that are particularly sensitive to calcification.

A. Biocompatible Articles

Relevant biocompatible articles include medical articles that contact bodily fluids for extended periods of time. The biocompatible articles can be made from the biocompatible materials described below. Relevant articles include, for example, implanted devices and percutaneous devices. Medical articles of particular interest are those susceptible to failure due to calcification.

Implanted devices broadly include articles that are fully implanted in a patient, i.e., are completely internal. Implanted devices include, for example, prostheses such as transplant organs, heart valve prostheses, pericardial patches, vascular grafts, biological conduits, annuloplasty rings, bone, skin, ligaments and tendons.

Percutaneous devices include articles that penetrate the skin, thereby extending from outside the body into the body. Percutaneous devices include without limitation catheters of various types. Catheters can be used for accessing various bodily systems such as the vascular system, the gastrointestinal tract, or the urinary system.

Suture can be used, for example, to secure sections of living tissue such as when closing a wound, to fasten together components within a medical article and/or to attach a medical article to living tissue. Suture can be made from a variety of materials such as collagen, polyesters, polypropylene, polyamides (nylon), cat gut, coated cat gut, polydioximone, polycaprolactone, polyhydroxy butyrate, polylactic acid and polyglycolic acid. Therefore, in certain applications, suture can be considered a component of a larger medical article. In other applications, suture can be considered an independent medical article. Since its structure allows for a variety of uses, suture cannot be classified exclusively as an implanted device or as a percutaneous device. Other articles also may be useful both as an implanted device and as a percutaneous device.

Certain medical devices when used for their intended purpose are located away from major blood vessels. Other medical devices when used for their intended purpose are associated with major blood vessels. In general, medical devices associated with major blood vessels have portions associated with high blood flow and other portions in regions of low blood flow, which are not in contact with blood flow through the vessel. Similarly, these medical devices can have portions of biocompatible material substantially removed from the blood flow that have an edge or the like within the vessel in a region of high blood flow or in a region with turbulent flow.

B. Biocompatible Materials

As noted above, the medical articles of interest include biocompatible materials. Many medical articles include several different types and/or separate portions of biocompatible material that are fabricated to form the medical article. Preferably, the anticalcific elemental metal associated with a portion or portions of biocompatible material is located at or near sections of the medical article susceptible to calcification. Tissue and polyurethane prosthetic valves are particularly susceptible to calcification.

Appropriate biocompatible materials include natural materials, synthetic materials and combinations thereof. Natural, i.e., biological, material for use in the invention includes relatively intact (cellular) tissue as well as decellularized tissue. These tissues may be obtained from, for example, natural heart valves; portions of natural heart valves such as roots, walls and leaflets; pericardial tissues such as pericardial patches; connective tissues; bypass grafts; tendons; ligaments; skin patches; blood vessels; cartilage; dura mater; skin; bone; umbilical tissues; and the like.

Natural tissues are derived from a particular animal species, typically mammalian, such as human, bovine, porcine, seal or kangaroo. These natural tissues generally include collagen-containing material. Natural tissue is typically, but not necessarily, soft tissue. Appropriate tissues also include tissue equivalents such as tissue-engineered material involving a cell-repopulated matrix, which can be formed from a polymer or from a decellularized natural tissue.

Biological tissues can be fixed by crosslinking. This provides mechanical stabilization, for example, by preventing enzymatic degradation of the tissue. Glutaraldehyde is typically used for fixation, but other fixatives can be used, such as epoxides, formaldehyde and other difunctional aldehydes. Biological materials can be used in either crosslinked or uncrosslinked form, depending on the type of tissue, the use and other factors.

Relevant synthetic materials include, for example, polymers and ceramics. Appropriate ceramics include, without limitation, hydroxyapatite, alumina and pyrolytic carbon. Polymeric materials can be fabricated from synthetic polymers as well as from purified biological polymers. Appropriate synthetic materials include hydrogels and other synthetic materials that cannot withstand severe dehydration.

Appropriate synthetic polymers include without limitation polyamides (e.g., nylon), polyesters, polystyrenes, polyacrylates, vinyl polymers (e.g., polyethylene, polytetrafluoroethylene, polypropylene and poly vinyl chloride), polycarbonates, polyurethanes, poly dimethyl siloxanes, cellulose acetates, polymethyl methacrylates, ethylene vinyl acetates, polysulfones, nitrocelluloses and similar copolymers. These synthetic polymeric materials can be woven into a mesh to form a matrix or substrate. Alternatively, the synthetic polymer materials can be molded or cast into appropriate forms.

Biological polymers can be naturally occurring or produced in vitro by, for example, fermentation and the like. Purified biological polymers can be appropriately formed into a substrate by techniques such as weaving, knitting, casting, molding, extrusion, cellular alignment and magnetic alignment. For a description of magnetic alignments see, for example, R. T. Tranquillo et al., Biomaterials 17:349–357 (1996), incorporated herein by reference. Suitable biological polymers include, without limitation, collagen, elastin, silk, keratin, gelatin, polyamino acids, cat gut sutures, polysaccharides (e.g., cellulose and starch) and copolymers thereof. The biological polymers can be resorbable.

Biocompatible materials can include a combination of the various natural materials and synthetic materials described above. The biocompatible materials also can include metal portions. Mechanical heart valves are relevant products, which generally are made from metallic and/or ceramic components, along with a sewing cuff and/or a vascular graft.

The biocompatible materials are combined to form the medical article. For example, a mechanical heart valve can include mechanical and ceramic components that are located within the blood flow path along with additional components for securing the valve. Referring to FIG. 1A, the cross section of one embodiment of a mechanical heart valve 100 is depicted. Heart valve 100 includes an orifice 102 that forms a blood flow path through the interior 104 of orifice 102. Heart valve 100 is depicted as a bileaflet valve with two leaflets or occluders 106, 108 that pivot between an open position and a closed position such that the blood flow path through orifice 102 is correspondingly open or closed.

Sewing cuff 110, which generally can be made of fabric, is located at the exterior 112 of orifice 102 substantially out of the path of blood flow. The sewing cuff is a potential site for calcification. Sewing cuff 110 can be surgically sutured to heart tissue to secure valve 100. The invention also includes other designs and/or types of mechanical heart valves.

Alternatively, heart valve prostheses can be based on synthetic polymer leaflets, as depicted in FIG. 1B. Heart valve prosthesis 120 includes a stent 122 that provides support for the leaflets. Stent 122 can be made from a variety of materials including, for example, polymers, metals and combinations thereof. Suitable synthetic polymers for use in forming stent 122 include, for example, thermoplastics such as polyolefins, polyesters, polyamides, polysulfones, acrylics, polyacrylonitriles, acetal polymers such as Delrin®, polyethers such as polyetheretherketone (PEEK), and polyaramides. Leaflets 124 and stent 122 can be made from synthetic polymers, which optionally can be bioresorbable, being made from polymers such as polyamino acids and/or polysaccharides. Preferred nonresorbable polymers for incorporation into leaflets 124 include, for example, polyurethanes, polyether/polyurethane block copolymers, silicone elastomers, polytetrafluoroethylene and sulfur crosslinked 1-hexene/methyl hexadiene copolymer. Prosthesis 120 includes a fabric sewing cuff 126.

Referring to FIG. 2, heart valve prosthesis 130 is attached to a vascular graft 132 to configure the valve as an aortic valved graft. Vascular graft 132 can replace a portion of the blood vessel leading to valve 130. Heart valve prostheses, configured to replace different natural valves such as pulmonary valves, aortic valves, mitral valves and tricuspid valves, generally include similar, appropriately located sewing cuffs 134 substantially outside of the blood flow.

Referring to FIG. 3, annuloplasty ring 150 can include a frame 152 covered with a layer of fabric 154 such as woven or knitted polyester. Fabric 154 can cover the entire outer surface of annuloplasty ring 150. Annuloplasty ring 150 can be implanted to support the base of a native heart valve. Annuloplasty ring 150 is located substantially outside of the direct blood flow.

An embodiment of a bioprosthetic heart valve 180 including a tissue component 182 is depicted in FIG. 4. The tissue component includes three leaflets 184, 186, 188 that function to open and close the valve and cylindrical section 190 that defines a blood flow path through the interior of the cylindrical section 190 with flow controlled by the leaflets 184, 186, 188. Leaflets 184, 186, 188 are attached to cylindrical section 190 at commissures. Cylindrical section 190 includes an annular portion and three commissure supports. The outside of cylindrical section 190 is covered with fabric 192. Fabric 192 can be attached with suture 194 or using nonsuture fastening approaches. Fabric 192 is outside of the blood flow in a low flow region when the valve 180 is in place within the patient. As depicted in the insert of FIG. 4, suture 194 can include a coating 196 of anticalcific elemental metal.

C. Deposit of Anticalcific Elemental Metal

The approaches for applying deposits of anticalcific metal to biocompatible materials can be broadly classified according to whether the deposition takes place from a vapor phase or from a liquid phase. Anticalcific metals include, for example, aluminum, iron, magnesium, zinc, gallium, lanthanum and beryllium with aluminum, iron and magnesium being preferred. Various deposition approaches can be selected for use with particular types of biocompatible materials. For example, some methods may use conditions that are harsh with respect to certain materials such that the materials would be significantly degraded. In particular, tissue generally cannot withstand the conditions used for vapor phase metal deposition.

Vapor phase methods include, for example, vapor-deposition, sputtering and magnetron sputtering. Vapor phase techniques generally require varying degrees of vacuum, i.e., low pressures. Some materials may not tolerate the low pressures easily. Vapor based methods are particularly suitable for the deposition of anticalcific metal onto fabric. This coated fabric can be incorporated into any of the medical articles described above such as those depicted in FIGS. 1–4.

Vapor deposition can simply involve directing vaporized metal through an opening toward the substrate to be metalized. Vapor deposition preferably is performed using ion-beam-assisted deposition (IBAD) under high vacuum as described, for example, in U.S. Pat. No. 5,474,797 to Sioshansi et al., incorporated herein by reference. IBAD involves an evaporator that forms a vapor of the desired metal. The metal vapor is delivered to the substrate by a beam of ions formed from one or more gases.

Solution based methods for anticalcific metal deposition include chemical reduction and electroplating. Suitable chemical reducing agents include, for example, sodium borohydride, $H_2$ and CO for reduction of a variety of metals. Gaseous reducing agents can be bubbled through the solution. Suitable solvents are generally aqueous although other solvents, such as alcohol, can be used if the biocompatible material is not damaged by the solvent. When processing tissue, it is preferred to keep the pH between values of about 4 and about 11, and more preferably between about 7.0 and about 8.0, to the extent that the pH can be adjusted within the particular processing approach. Ionic strength can be adjusted, if desired, by the addition of inert salts, the identity of which generally depends on the nature of the deposition process and the corresponding compositions.

Electrochemical deposition involves the application of a voltage to a suitable biocompatible material, such as tissue, in order to electroplate, from a metal solution, elemental metal in contact with the biocompatible material. The biocompatible material functions as the cathode. The required voltage depends on the counter reaction and the concentrations of ions in solution. The selection of the metal salt influences the effectiveness of the plating process.

To determine the amount of metal to deposit, the rate of dissolution generally is a consideration. The environment in which the biocompatible material is placed can influence the rate of dissolution. Given a particular rate of dissolution, the amount of deposited metal establishes the length of time over which metal is available for calcium inhibition.

With any method of deposition, the amount of deposited metal should not interfere significantly with important functionality of the biocompatible material. If the conditions for depositing the elemental metal are relatively harsh, it may be desirable to limit the deposition time while accepting a corresponding decrease in deposited metal. With respect to the deposition, the amount of anticalcific metal generally is greater than about 0.01 mg per gram of dry biocompatible material, and preferably from about 0.05 mg to about 40 mg per gram of dry biocompatible material, and more preferably from about 0.1 mg to about 20 mg per gram of dry biocompatible material. When incorporated into a medical article, the proportion of elemental metal for the total quantity of biocompatible material can be less than the above range since some of the biocompatible material may not have deposits of elemental metal.

In general, the biocompatible material can be subjected to deposition of elemental metal prior to, during or after processing into a biocompatible article. For example, to form a tissue heart valve prosthesis with a fabric cover, the tissue component and the fabric can be separately subjected to deposition of anticalcific elemental metal using conditions suitable for each material. Similarly, only the tissue or only the fabric can be subjected to anticalcific metal deposition. Following the desired deposition of elemental metal, the tissue component and the fabric components can be combined. Alternatively, the tissue components and the fabric components can be formed into a biocompatible article followed by the deposition of anticalcific elemental metal on the article using a suitable method for both materials.

Multiple elemental metals can be deposited. For vapor phase techniques, the deposition of multiple metals can be performed sequentially or simultaneously. Generally, solution-based methods involve the sequential deposition of the elemental metals. In addition, different elemental metals can be incorporated onto different portions of one or more sections of biocompatible material for incorporation into a single medical article.

Multiple elemental metals can be deposited such that the different metals are or are not in electrical contact with each other. If the different metals are in electrical contact, the oxidation potential of one metal influences the rate of oxidation of the other metal. In this way, the rate of oxidation of one metal can be accelerated or slowed by the selection of the second metal. The second metal can be selected also to supply beneficial effects, as described below.

D. Combined Anticalcification Agents

Multiple anticalcific agents can be combined to obtain greater anticalcific activity than that provided by one of the agents alone. The additional anticalcific agents can be elemental metal, other types of chemical compositions or combinations thereof. The deposition of multiple elemental metals has been described above, where two or more elemental metals can have anticalcific properties.

All of the considerations described above apply equally if multiple elemental metals have anticalcific properties. For example, if the metals are in electrical contact, one metal generally is stabilized in its elemental form while enhancing the oxidation of the other metal. Therefore, the stabilized metal may not be as effective as an anticalcific agent while the other metal is present. Even if the elemental metals are not in direct electrical contact, the presence of the second elemental metal may influence the oxidation rate and corresponding effectiveness as an anticalcific agent. Two or more anticalcific elemental metals can be combined with one or more additional elemental metals that lack any appreciable anticalcific effectiveness. The additional elemental metal or metals can introduce a different activity such as antimicrobial effectiveness, or can adjust the delivery or adhesion of the anticalcific elemental metals.

Multiple metals can be placed in successive layers, the metals can be simultaneously deposited to create an amorphous surface, and/or they can be patterned onto the substrate such that each metal contacts a selected portion of the substrate. Solution phase techniques generally are not used to pattern the metals unless the metals are deposited onto portions of substrate that are later attached to form the pattern. The order of sequential deposition may be influenced by the method used to deposit the elemental metals if, for example, one elemental metal is unstable during the deposition of the second metal. The placement of the multiple metals generally is influenced by the effect on the anticalcific effectiveness resulting from the particular relationship between the metals.

An anticalcific elemental metal can be combined with other chemical forms of anticalcific agents. For example, the biocompatible material can be treated with a solution of a compound including anticalcific metal ions such as $Al^{+3}$, $Mg^{+2}$ or $Fe^{+3}$. The direct application of metal ions can provide a more immediate anticalcific effect while the elemental metal provides longer term anticalcific activity. Metal salt concentrations of the salt solutions generally are between 0.00001 and 0.1 molar, and preferably between 0.001 and 0.1 molar. Appropriate salts include, for example, aluminum chloride, aluminum chlorate, aluminum lactate, aluminum potassium sulfate, aluminum nitrate, ferric chloride, ferric nitrate, ferric bromide, ferric sodium edentate, ferric sulfate, and ferric formate.

The metal salts also can be incorporated into a polymer matrix used in the prosthesis. The metal salts are preferably added during the polymerization step so that they are incorporated into the polymer matrix. In this way, the calcification inhibitor is released at a controlled rate over an extended period of time.

In addition, anticalcific metal ions can be supplied to the biocompatible material reversibly bound to exogenous storage structures. Preferred exogenous storage structures for the delivery of $Al^{+3}$ and $Fe^{+3}$ include, for example, ferritin and related metal storage proteins. The ferritin can be attached to tissue and other substrates by chemical crosslinking and the like. The delivery of anticalcific metal cations using exogenous storage structures is described in copending and commonly assigned U.S. patent applications Ser. Nos. 08/595,402 and 08/690,661, both of which are incorporated herein by reference.

Calcium ion chelators preferably at concentrations between approximately 0.00001 M and approximately 0.1 M can be added to the metal salt solutions prior to treatment. For example, citrate salts and citric acid have been found to enhance synergistically the calcification inhibition effect of $Al^{+3}$ and $Fe^{+3}$ ions. Similarly, other calcium ion chelators such as diphosphonate salts, including without limitation ethanehydroxydiphosphonate (EHDP or etidronate) and aminopropanehydroxydiphosphonate, also produce a synergistic improvement in the anticalcification effect of the $Al^{+3}$ and $Fe^{+3}$ ions. Higher or lower concentrations can be used in particular applications.

The order of application of multiple anticalcific agents can influence the effectiveness of a particular agent. The particular application techniques can influence the selected order of application such that one agent is not rendered ineffective by the deposition of a second agent. These factors can be examined empirically, if desired.

E. Other Biological Agents

Metals including Au, Ag, Pt, Pd, Ir, Cu, Sn, Sb, Bi and Zn are known to yield antimicrobial activity, with silver being preferred. When depositing multiple elemental metals, one or more of the metal can be selected for its antimicrobial efficacy. In this way, the deposits of elemental metal can inhibit calcification as well as inhibit infection. Electrical contact of the elemental metals influences their respective oxidation rates and their corresponding efficacies.

In addition, metal compounds with antimicrobial activity can be deposited. These metal compounds can be deposited by precipitation of the compound from a solution of a corresponding soluble metal compound by the addition of a precipitation agent, generally an appropriate anion or a reducing agent to form a lower oxidation state metal ion. Deposition of antimicrobial metal compounds is described further in copending and commonly assigned U.S. patent application Ser. No. 08/974,992, incorporated herein by reference.

In addition, there are certain situations where other biological activities are desirable. In these situations, materials can be made by forming a bioactive coating on a base material, where the bioactive coating can include, for example, cell adhesion molecules, anticoagulants such as heparin and hirudin, or growth factors, and combinations thereof.

The order of application of the anticalcific metal and bioactive coating can be selected based on compatibility of the application methods. If appropriate, the anticalcific metal and the bioactive coating can be added simultaneously. Performance may be influenced by the order of application of the different active agents, and in such cases, the order of application can be selected based on performance considerations. Empirical evaluation of these factors can be performed, if desired.

F. Storage, Packaging, Distribution and Use

Following deposition of the desired anticalcific elemental metal, the biocompatible material, possibly formed into a medical article, is stored. Preferred storage techniques minimize the risk of microbial contamination. For example, the biocompatible material can be stored in a sealed container with an aqueous glutaraldehyde solution. In a sealed container, the biocompatible material is not subjected to a continuous supply of fluids. As a result, corrosion of the anticalcific elemental metal may be limited.

Due consideration should be given to possible loss of the anticalcific elemental metal or other active agents over time. If excessive corrosion is a possibility, the storage time can be appropriately limited to keep the corrosion to an acceptable level. Additives can be added to reduce the corrosion. For example, antioxidants such as ascorbic acid can be added.

For distribution, the medical articles are placed in sealed and sterile containers. The containers generally are dated such that the date reflects the maximum advisable storage time accounting for possible degradation of anticalcific and other agents as well as other factors. The containers are distributed to health care professionals for use in appropriate medical procedures such as surgical implantation of a prosthesis and the like. The surgical implantation of heart valves, such as those depicted in FIGS. 1A, 1B and 4, is of particular interest.

The resulting prostheses with associated anticalcific metals have advantages with respect to long term durability. The anticalcific ions can be effective to reduce calcification of tissue either by depositing the metal on the tissue or by associating an anticalcific metal coated material such as fabric with the tissue. The method can involve relatively large quantities of anticalcifics. The release rate of the anticalcific ions can be adjusted by the selection of metal or combination of metals or by pretreating the metal. Furthermore, anticalcifics can be associated with polyurethane heart valve prostheses and suture. Anticalcific coated fabric and/or suture can be associated with homografts or commercially available heart valve prostheses. The medical articles of the invention can include antimicrobial elemental metal and/or an antimicrobial metal composition along with the anticalcific elemental metal to reduce the risk of infection as well as reducing calcification.

EXAMPLES

Example 1—Washout Studies

This example involves a determination of the rate of dissolution of aluminum from a coated fabric when in contact with blood serum.

Four pieces each of three types of fabric were used. Each piece of fabric was about 1 square centimeter. The first fabric, the control fabric, was a woven double velour Dacron-polyester fabric obtained from Meadox Medicals, Inc. (Lot 186116). The second fabric (Al fabric) was identical to the control fabric except for a coating of elemental aluminum applied using an Ion Beam Assisted Deposition (IBAD) Process such as described in U.S. Pat. No. 5,474,797, supra. In the IBAD process, the substrate is mounted on a rotating substrate holder within a vacuum chamber. A beam of energetic ions directs evaporated metal atoms at the substrate surface to form a coating of elemental metal on the substrate. The IBAD aluminum deposition was performed by Spire Corp., Bedford, Mass.

The third fabric (Al/Ag fabric) first received an antimicrobial coating including elemental silver, titanium and palladium using a process developed by Spire Corp. The three layer, metal coating is described in U.S. Pat. No. 5,520,664 to Bricault Jr., et al., incorporated herein by reference. Then, the silver coated fabric received a further coating of aluminum using the IBAD process, as described above. The aluminum presumably was in electrical contact with the silver, titanium and palladium metals.

All twelve fabric pieces were weighed after they were excised. Then, the twelve fabric pieces were sterilized with steam. Nine-500 ml bottles of bovine serum (Sigma Chemical, St. Louis, Mo.) were obtained. Five milliliters of serum were removed antiseptically from each bottle and used as a "zero day" control. Each of nine sterilized fabric samples was transferred antiseptically under a laminar flow hood into a separate serum bottle. After the fabric samples were placed into serum bottles, the serum bottles were placed onto a shaking water bath (Environ Shaker™, Lab-Line, Melrose Park, Ill.) set at about 37° C. and about 100 RPM.

Figure 5:
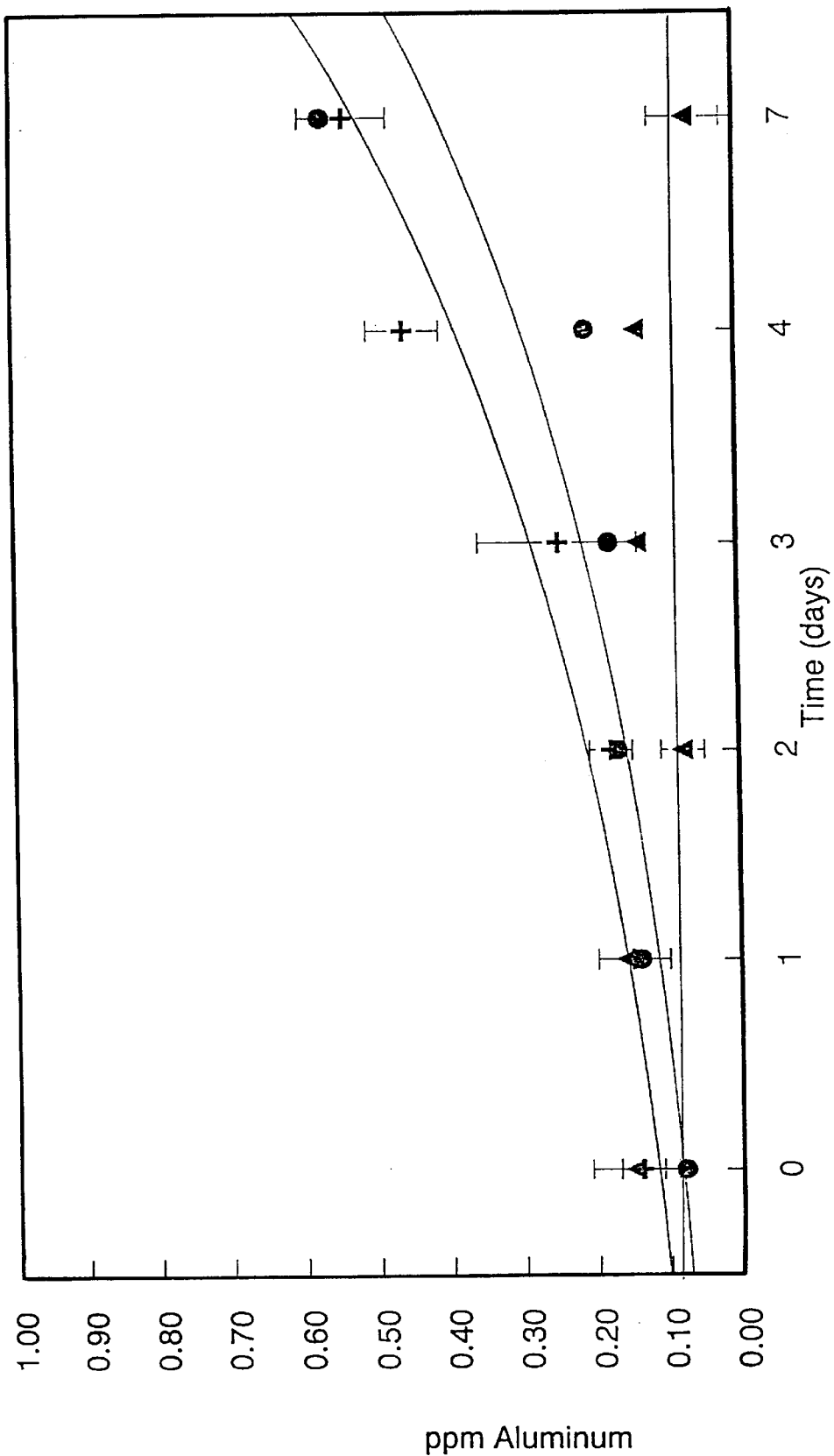
FIG. 5 is a plot of aluminum concentration in parts per million in a bovine serum solution as a function of time where the solution contains one of three fabric samples.

Following 1, 2, 3, 4 and 7 days of incubation, 5 ml samples were removed antiseptically from each bottle. The liquid samples were placed separately into 25 ml vials. The liquid controls and liquid samples were subjected to analytical analysis for aluminum content using an ICP-AES AtomScan 16™ (Thermo Jarrell Ash Corp., Franklin, Mass.). The results are presented in Table 1 including averages and the standard deviation (S.D.), and the average results are plotted in FIG. 5.

TABLE 1

| Time | Al (ppm) | | | | | Al (mg/ml) | |
|---|---|---|---|---|---|---|---|
| (days) | Sample #1 | Sample #2 | Sample #3 | Average | S.D. | Average | S.D. |
| Al/Ag Fabric | | | | | | | |
| 0 | 0.1076 | 0.1244 | 0.1734 | 0.14 | 0.03 | 2.70E-04 | 6.64E-05 |
| 1 | 0.1118 | 0.1179 | 0.2095 | 0.15 | 0.05 | 2.93E-04 | 1.09E-04 |
| 2 | 0.1619 | 0.1675 | 0.2150 | 0.18 | 0.03 | 3.63E-04 | 5.84E-05 |
| 3 | 0.2100 | 0.1722 | 0.3790 | 0.25 | 0.11 | 5.07E-04 | 2.21E-04 |
| 4 | 0.4316 | 0.4289 | 0.5162 | 0.46 | 0.05 | 9.18E-04 | 9.93E-05 |
| 7 | 0.4696 | 0.5601 | 0.5923 | 0.54 | 0.06 | 1.08E-03 | 1.27E-04 |
| Al Fabric | | | | | | | |
| 0 | 0.0713 | 0.0899 | 0.0796 | 0.08 | 0.00 | 1.61E-04 | 3.21E-07 |
| 1 | 0.13 | 0.1518 | 0.1491 | 0.14 | 0.01 | 2.89E-04 | 2.01E-05 |
| 2 | 0.15 | 0.1741 | 0.1692 | 0.17 | 0.01 | 3.30E-04 | 2.36E-05 |
| 3 | 0.18 | 0.1857 | 0.1716 | 0.18 | 0.01 | 3.57E-04 | 1.42E-05 |
| 4 | 0.20 | 0.2274 | 0.1929 | 0.21 | 0.02 | 4.10E-04 | 3.85E-05 |
| 7 | 0.56 | 0.5870 | 0.5670 | 0.57 | 0.01 | 1.14E-03 | 2.59E-05 |
| Control Fabric | | | | | | | |
| 0 | 0.21 | 0.1521 | 0.0845 | 0.15 | 0.06 | 2.97E-04 | 1.25E-04 |
| 1 | 0.18 | 0.15 | 0.1376 | 0.16 | 0.02 | 3.13E-04 | 4.58E-05 |
| 2 | 0.0543 | 0.077 | 0.1138 | 0.08 | 0.03 | 1.63E-04 | 6.01E-05 |
| 3 | 0.1297 | 0.1716 | 0.1276 | 0.14 | 0.02 | 2.86E-04 | 4.96E-05 |
| 4 | 0.142 | 0.1506 | 0.1334 | 0.14 | 0.01 | 2.84E-04 | 1.72E-05 |
| 7 | 0.1197 | 0.0636 | 0.0293 | 0.07 | 0.05 | 1.42E-04 | 9.13E-05 |

Significant concentrations of aluminum were present in the serum with both the Al fabric and the Al/Ag fabric by 4 days within the serum. While the Al/Ag fabric released greater amounts of aluminum than the Al fabric after 4 days within the serum, by seven days the Al fabric and the Al/Ag fabric released comparable quantities of aluminum into the serum.

Following seven days of incubation, the fabric samples were removed from the serum and dried with a lyophilizer. The fabric samples along with comparable pieces that had not been placed in serum were analyzed for aluminum content. To analyze the fabric samples, the fabric pieces were hydrolyzed in nitric acid. Then, measurements were made using ICP-AES, as described above. The results are presented in Table 2, where the weights were measured before serum contact.

TABLE 2

| Sample | wt (mg) | Al (ppm) | Al (mg/g) |
|---|---|---|---|
| Al/Ag Fabric | | | |
| No Serum Contact | | | |
| 1 | 5.24 | 0.61 | 2.90 |
| 2 | 6.61 | 0.73 | 2.75 |
| 3 | 6.19 | 0.74 | 2.99 |
| | | | 2.88 (Avg.) |
| | | | 0.12 (S.D.) |
| Post Serum Contact | | | |
| 1 | 7.88 | 0.70 | 2.23 |
| 2 | 12.08 | 1.08 | 2.23 |
| 3 | 10.60 | 0.63 | 1.50 |
| | | | 1.99 (Ave) |
| | | | 0.42 (S.D.) |
| Al Fabric | | | |
| No Serum Contact | | | |
| 1 | 7.76 | 2.72 | 8.76 |
| 2 | 10.85 | 4.01 | 9.23 |
| 3 | 10.05 | 3.81 | 9.48 |
| | | | 9.16 (Ave) |
| | | | 0.36 (S.D.) |
| Post Serum Contact | | | |
| 1 | 13.26 | 4.05 | 7.63 |
| 2 | 10.45 | 3.59 | 8.59 |
| 3 | 9.25 | 2.67 | 7.21 |
| | | | 7.81 (Ave) |
| | | | 0.71 (S.D.) |
| Control Fabric | | | |
| No Serum Contact | | | |
| 1 | 13.82 | 0.04 | 0.08 |
| 2 | 17.09 | 0.04 | 0.05 |
| 3 | 14.98 | 0.04 | 0.06 |
| | | | 0.07 (Ave) |
| | | | 0.01 (S.D.) |
| Post Serum Contact | | | |
| 1 | 17.29 | 0.03 | 0.05 |
| 2 | 17.53 | 0.03 | 0.04 |
| 3 | 17.36 | 0.02 | 0.04 |
| | | | 0.04 (Ave) |
| | | | 0.01 (S.D.) |

The results in Table 2 indicate that Al was released into the serum.

Example 2—In vivo Studies

This example demonstrates an in vivo reduction of calcification of aluminum coated fabric. Two sets of experiments were performed using similar procedures.

Samples were prepared from 8 mm punches of porcine aortic root tissue. The tissue samples were crosslinked in buffered 0.5% glutaraldehyde solutions. In the first study, twelve samples were used. Six samples were sewn to aluminum coated fabric, and six samples were sewn to polyester fabric, as controls. After sewing the tissue to the fabric, the samples were placed in buffered glutaraldehyde.

For the second study, a total of thirty six tissue samples were used. A piece of fabric was sutured to each tissue sample. Twelve tissue samples were sutured to plain, polyester fabric. Twelve tissue samples were sutured to aluminum coated polyester fabric, where the Al fabric was prepared as described in Example 1. The remaining twelve tissue samples were sutured to aluminum/silver coated fabric, where the Al/Ag fabric was prepared as described in Example 1. All the samples were stored for twelve days in a HEPES buffered saline solution containing 0.5% glutaraldehyde prior to implantation.

Prior to implantation, all of the samples were rinsed three times for 2–5 minutes using sterile saline. The 12 samples in the first study were placed subdermally in the backs of three juvenile male rats using color coded suture. The thirty six samples in the second study were placed subcutaneously in the backs of six juvenile male rats (two of each type per rat) using color codes suture. The samples were removed after 21 days (first study) or 26 days (second study). Following removal the samples were placed in 0.9 percent saline (NaCl in $H_2O$) prior to analysis.

For analysis, each tissue sample was sectioned in half. One half of each sample was cleaned of host capsule. For the first study, the fabric was removed from all the samples. For the second study, the fabric was removed from the control samples while the fabric was left attached to the other samples. The tissue and fabric were placed into a polypropylene test tube (separately if detached) and lyophilized. For elemental analysis, the dried samples were hydrolyzed in nitric acid. Elemental analysis was performed by ICP-AES, as described above. The results of the elemental analysis are presented in Table 3 (first study) and Table 4 (second study). For the second study, the calculations were adjusted to remove approximately the contribution of the fabric, which calcifies significantly less relative to the calcification of the tissue.

TABLE 3

| | Weight | CALCIUM | | ALUMINUM | |
|---|---|---|---|---|---|
| Sample | mg | ppm | mg/g | ppm | mg/g |
| Control-Tissue | | | | | |
| 1 | 23.6 | 55.29 | 58.57 | 0.0486 | 0.05 |
| 2 | 22.1 | 50.8 | 57.47 | 0.0507 | 0.06 |
| 3 | 20.6 | 30.19 | 36.64 | 0.0521 | 0.06 |
| 4 | 15.8 | 43.04 | 68.10 | 0.0516 | 0.08 |
| 5 | 24.7 | 45.65 | 46.20 | 0.0496 | 0.05 |
| 6 | 18.8 | 48.81 | 64.91 | 0.0462 | 0.06 |
| | average= | 55.31 | | | 0.06 |
| | std dev= | 11.85 | | | 0.01 |
| Al-Tissue | | | | | |
| 1 | 20.6 | 32.82 | 39.83 | 0.0621 | 0.08 |
| 2 | 18.2 | 36.13 | 49.63 | 0.0554 | 0.08 |
| 3 | 19.7 | 31.86 | 40.43 | 0.0564 | 0.07 |
| 4 | 15.2 | 23.34 | 38.29 | 0.0446 | 0.07 |
| 5 | 18.2 | 35.12 | 48.24 | 0.0641 | 0.09 |
| 6 | 22.3 | 40.64 | 45.56 | 0.0627 | 0.07 |
| | average= | 43.68 | | | 0.08 |
| | std dev= | 4.76 | | | 0.01 |
| Al-Fabric | | | | | |
| 1 | 3.5 | 0.0913 | 0.65 | 0.7272 | 5.19 |
| 2 | 3.3 | 0.0644 | 0.49 | 0.7267 | 5.51 |
| 3 | 3.6 | 0.1293 | 0.90 | 0.7341 | 5.10 |
| 4 | 2 | 0.0461 | 0.58 | 0.414 | 5.18 |
| 5 | 1.9 | 0.0289 | 0.38 | 0.4729 | 6.22 |
| 6 | 3.4 | 0.0762 | 0.56 | 0.7755 | 5.70 |
| | average= | | 0.59 | | 5.48 |
| | std dev= | | 0.18 | | 0.48 |

TABLE 4

| Sample | Weight mg | ALUMINUM ppm | ALUMINUM mg/g | CALCIUM ppm | CALCIUM mg/g |
|---|---|---|---|---|---|
| Control-Tissue | | | | | |
| 1 | 31.75 | 0.0254 | 0.02 | 98.04 | 77.20 |
| 2 | 25.78 | 0.03 | 0.03 | 64.89 | 62.93 |
| 3 | 18.22 | 0.03 | 0.04 | 59.74 | 81.97 |
| 4 | 20.43 | 0.04 | 0.04 | 63.08 | 77.19 |
| 5 | 20.52 | 0.03 | 0.03 | 47.84 | 58.28 |
| 6 | 25.21 | 0.03 | 0.03 | 68.19 | 67.62 |
| 7 | 22.44 | 0.0328 | 0.04 | 54.5 | 60.72 |
| 8 | 19.74 | 0.0347 | 0.04 | 68.79 | 87.12 |
| 9 | 26.16 | 0.031 | 0.03 | 72.43 | 69.22 |
| 10 | 30.33 | 0.0325 | 0.03 | 67.69 | 55.79 |
| 11 | 15.24 | 0.0269 | 0.04 | 46.14 | 75.69 |
| 12 | 24.17 | 0.0365 | 0.04 | 47.59 | 49.22 |
| average= | | | 0.03 | | 68.58 |
| std dev= | | | 0.01 | | 11.53 |
| Al/Ag | | | | | |
| 1 | 23.69 | 0.88 | 0.93 | 33.10 | 42.11 |
| 2 | 20.72 | 0.08 | 0.10 | 42.85 | 64.22 |
| 3 | 27.22 | 0.09 | 0.08 | 25.94 | 27.98 |
| 4 | 20.97 | 0.07 | 0.08 | 31.27 | 46.18 |
| 5 | 27.21 | 0.12 | 0.11 | 35.95 | 38.79 |
| 6 | 21.69 | 0.08 | 0.09 | 34.39 | 48.71 |
| 7 | 25.71 | 0.11 | 0.10 | 25.42 | 29.33 |
| 8 | 26.93 | 0.07 | 0.07 | 45.16 | 49.32 |
| 9 | 22.03 | 0.09 | 0.18 | 36.62 | 50.89 |
| 10 | 19.99 | 0.08 | 0.10 | 19.64 | 30.78 |
| 11 | 22.57 | 0.08 | 0.08 | 25.36 | 34.21 |
| 12 | 23.06 | 0.09 | 0.10 | 29.93 | 39.34 |
| average= | | | 0.16 | | 41.82 |
| std dev= | | | 0.24 | | 10.66 |
| Al | | | | | |
| 1 | 33.41 | 0.8159 | 0.61 | 54.2 | 46.14 |
| 2 | 21.83 | 0.77 | 0.88 | 8.96 | 12.59 |
| 3 | 28.2 | 0.77 | 0.68 | 34.69 | 35.90 |
| 4 | 20.12 | 0.58 | 0.71 | 43.19 | 67.15 |
| 5 | 31.78 | 0.58 | 0.46 | 30.68 | 27.65 |
| 6 | 29.73 | 0.78 | 0.65 | 33.79 | 32.88 |
| 7 | 24.65 | 0.5641 | 0.57 | 16.3 | 19.77 |
| 8 | 18.19 | 0.0638 | 0.09 | 20.99 | 37.08 |
| 9 | 22.79 | 0.3745 | 0.41 | 31.73 | 42.31 |
| 10 | 22.31 | 0.5504 | 0.62 | 34.81 | 47.63 |
| 11 | 18.12 | 0.4201 | 0.58 | 13.59 | 24.13 |
| 12 | 21.96 | 0.6577 | 0.75 | 35.2 | 49.11 |
| average= | | | 0.59 | | 36.86 |
| std dev= | | | 0.20 | | 14.91 |

The results from the first study are at the edge of statistical significance with respect to demonstrating calcium reduction. The results from the second study do show clear statistical reductions in calcification for tissue associated with aluminum coated fabric. The improvements observed in the second study relative to the first study may be due to the storage of the samples for twelve days in a saline buffered glutaraldehyde solution prior to implantation. The extended period of time prior to implantation may have accelerated the corrosion process making more anticalcification ions present.

Figure 6:
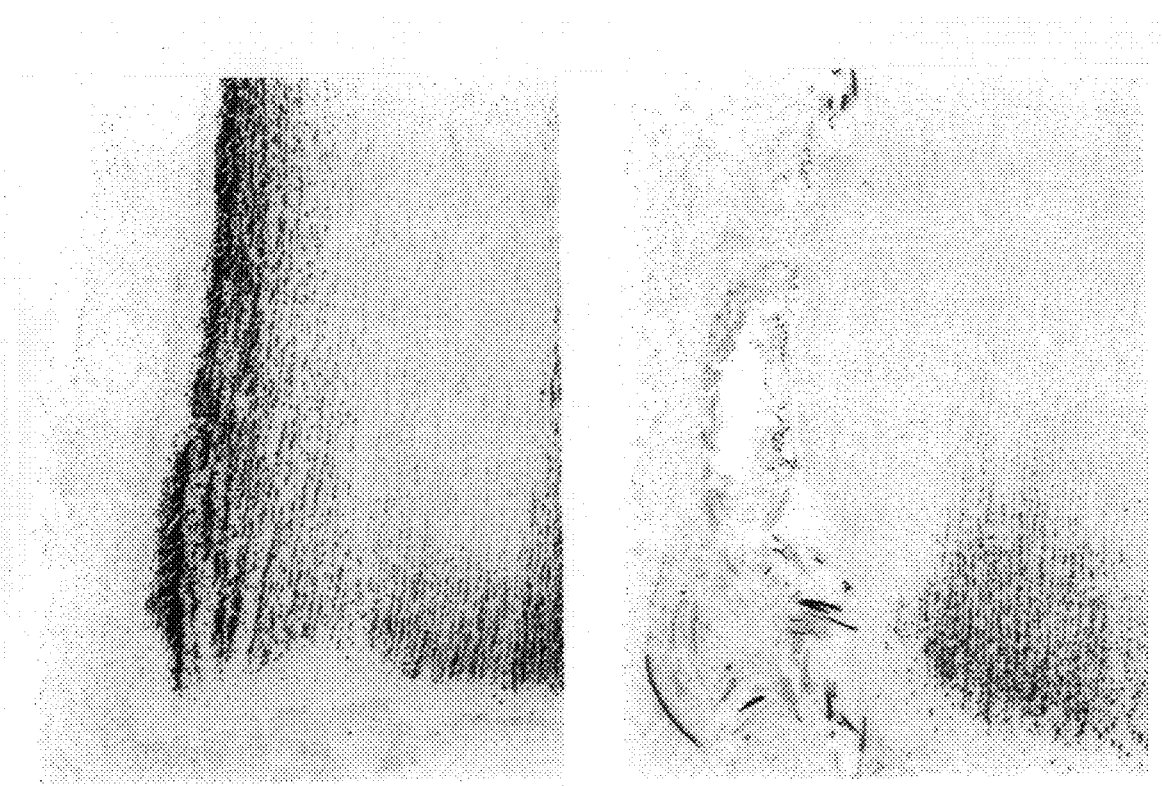
FIG. 6 is a collection of two photographs (40× magnification) of tissue following 21 days of subdermal implantation in the back of a rat where the tissue was stained such that calcium appears dark: A) one surface was covered with aluminum deposited fabric; B) control tissue sample.

The second half of each sample was placed in 10% buffered formalin (first study) or HEPES buffered-0.5% glutaraldehyde solution (second study) prior to histological examination. The histological analyses were performed using von Kossa stain. Exemplary photomicrographs from the first study are shown in FIG. 6. Referring to FIG. 6A, the control tissue had a band of continuous calcification at the outer surface. Referring to FIG. 6B, a transition area can be seen between the calcified and noncalcified tissue on the fabric coated side of the sample. Calcification was significantly, if not completely, mitigated in the areas where the fabric was sutured to the tissue. In the center of the sample, where there was no suture, some calcification near the surface of the sample occurred.

Figure 7:
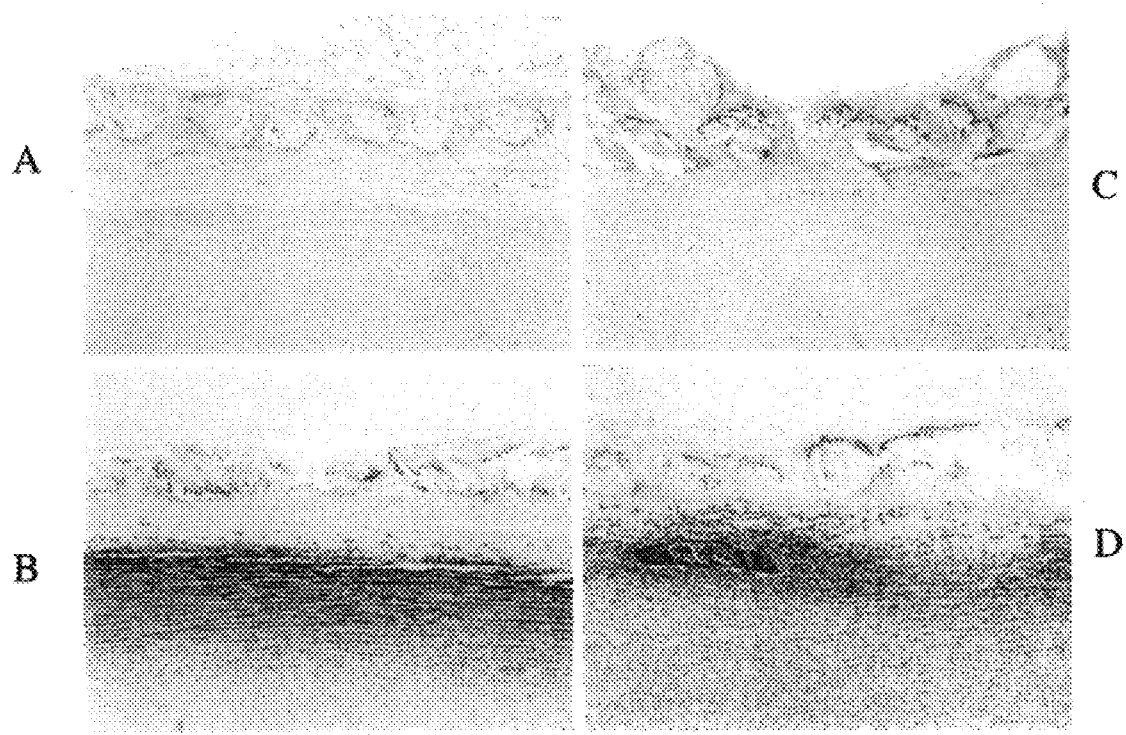
FIG. 7 is a collection of four photographs of tissue following 26 days of subdermal implantation in the back of a rat where the tissue was stained such that calcium appears dark: A) one surface was covered with aluminum deposited fabric; B) one surface was covered with plain polyester fabric; C) one surface was covered with aluminum/silver deposited fabric; D) one surface was covered with plain polyester fabric.

Exemplary micrographs from the second study are shown in FIG. 7. It can be seen that the samples with Al fabric (FIG. 7A) and Al/Ag fabric (FIG. 7C) have less calcium, shown in dark, deposited in the fabric side of the tissue than deposited in the corresponding control fabric samples (FIGS. 7B and 7D).

Example 3—Pretreated Surface—Washout Studies

This example involves evaluating the degree of ionization of an aluminum coating following pretreatment of the aluminum coating.

Washout studies were performed with 24 strips of fabric each about 2 cm wide and about 3.75 cm long. Half of the strips were Al coated fabric and the other half were Al/Ag coated fabric identical to the comparable fabric used in Example 1. Three strips of each type received no pretreatment and served as controls. Another three strips of each type received 20 cuts each all the way through the fabric to increase the surface area exposed to oxidation. The cuts were made ten per edge across about ¾ of the width of the fabric strip.

Also, three strips of each type were exposed to 3.2% peroxyacetic acid for about 5 minutes. The three strips of each type were exposed together to 12.5 ml of the peroxyacetic acid. The 3.2% peroxyacetic acid was prepared by diluting 2.5 mls of a stock solution of 32% by weight peroxyacetic acid, Aldrich Chemical Co., Milwaukee, Wis., to 25 mls with purified water.

The remaining three strips of each type were exposed to 10% HCl for 5 minutes. Again, the three strips of each type were exposed together to 12.5 mls of acid. The 10% HCl solution was prepared by diluting 6.5 mls of concentrated HCl, Fisher Chemical, Fair Lawn, N.J., with sufficient purified water to fill a 25 ml volumetric flask. The strips treated with either peroxyacetic acid or hydrochloric acid were immediately removed from the respective acid and rinsed three times each with 150 ml of purified water with the second and third rinses taking 5 minutes and 10 minutes, respectively.

The washout study was performed using the 24 fabric strips. Each strip was placed in 1 liter plastic containers with 500 mls of 0.9% (NaCl) sterile saline from Baxter, Deerfield, Ill. The containers with the strips and saline were placed on a shaker and incubated at 37° C. At 0, 3, 5 and 7 days, 5 mls of liquid was removed from each container and analyzed for aluminum content. The results for the Al coated fabric are presented in Table 5, and the results for the Al/Ag coated fabrics are presented in Table 6.

TABLE 5

| | Al Fabric | | | | |
|---|---|---|---|---|---|
| | Al (ppm) | | | | |
| Time (days) | Sample #1 | Sample #2 | Sample #3 | Average | S.D. |
| Control | | | | | |
| 0 | 0.10 | 0.10 | 0.09 | 0.10 | 0.00 |
| 3 | 0.12 | 0.12 | 0.14 | 0.12 | 0.01 |
| 5 | 0.16 | 0.14 | 0.13 | 0.14 | 0.01 |

TABLE 5-continued

Al Fabric

Al (ppm)

| Time (days) | Sample #1 | Sample #2 | Sample #3 | Average | S.D. |
|---|---|---|---|---|---|
| 7 | 0.22 | 0.21 | 0.18 | 0.20 | 0.00 |
| Cut | | | | | |
| 0 | 0.09 | 0.07 | 0.08 | 0.08 | 0.01 |
| 3 | 0.09 | 0.08 | 0.16 | 0.11 | 0.04 |
| 5 | 0.10 | 0.10 | 0.19 | 0.13 | 0.05 |
| 7 | 0.15 | 0.12 | 0.22 | 0.16 | 0.00 |
| Peroxyacetic Acid | | | | | |
| 0 | 0.10 | 0.09 | 0.09 | 0.09 | 0.01 |
| 3 | 0.12 | 0.09 | 0.10 | 0.10 | 0.02 |
| 5 | 0.13 | 0.13 | 0.13 | 0.13 | 0.00 |
| 7 | 0.35 | 0.38 | 0.32 | 0.35 | 0.03 |
| Hydrochloric Acid | | | | | |
| 0 | 0.10 | 0.09 | 0.09 | 0.09 | 0.00 |
| 3 | 0.15 | 0.10 | 0.11 | 0.12 | 0.03 |
| 5 | 0.23 | 0.17 | 0.12 | 0.17 | 0.05 |
| 7 | 0.33 | 0.32 | 0.28 | 0.31 | 0.03 |

TABLE 6

Al/Ag Fabric

Al (ppm)

| Time (days) | Sample #1 | Sample #2 | Sample #3 | Average | S.D. |
|---|---|---|---|---|---|
| Control | | | | | |
| 0 | 0.08 | 0.11 | 0.07 | 0.09 | 0.02 |
| 3 | 0.07 | 0.13 | 0.11 | 0.10 | 0.03 |
| 5 | 0.16 | 0.13 | 0.12 | 0.14 | 0.02 |
| 7 | 0.48 | 0.46 | 0.43 | 0.46 | 0.02 |
| Cut | | | | | |
| 0 | 0.08 | 0.09 | 0.09 | 0.09 | 0.00 |
| 3 | 0.15 | 0.13 | 0.11 | 0.13 | 0.02 |
| 5 | 0.17 | 0.14 | 0.16 | 0.15 | 0.01 |
| 7 | 0.54 | 0.42 | 0.41 | 0.46 | 0.07 |
| Peroxyacetic Acid | | | | | |
| 0 | 0.12 | 0.08 | 0.10 | 0.10 | 0.00 |
| 3 | 0.21 | 0.16 | 0.15 | 0.17 | 0.03 |
| 5 | 0.21 | 0.17 | 0.21 | 0.20 | 0.02 |
| 7 | 0.51 | 0.55 | 0.46 | 0.51 | 0.04 |
| Hydrochloric Acid | | | | | |
| 0 | 0.13 | 0.10 | 0.07 | 0.10 | 0.03 |
| 3 | 0.19 | 0.20 | 0.10 | 0.16 | 0.06 |
| 5 | 0.23 | 0.22 | 0.19 | 0.21 | 0.02 |
| 7 | 0.48 | 0.46 | 0.56 | 0.50 | 0.05 |

Note that the acid pretreatments significantly increase the ionization of the Al coated fabric but not the Al/Ag coated fabric. Contrary to the results in Example 1, the Al/Ag fabric resulted in greater aluminum ionization than observed for the Al coated fabric. This difference may be due to the fact that the washout study in Example 3 was performed using saline rather than bovine serum. Bovine serum contains biological chelators such as transferring which may accelerate the delivery of metals into solution.

The embodiments described above are intended to be exemplary and not limiting. Additional embodiments are within the claims.

What is claimed is:

1. A medical article comprising tissue, said tissue comprising a deposit of anticalcific, elemental metal.

2. The medical article of claim 1 wherein said anticalcific elemental metal is selected from the group consisting of aluminum, iron, magnesium and combinations thereof.

3. The medical article of claim 1 wherein said medical article is a heart valve prosthesis.

4. The medical article of claim 1 wherein said tissue comprises crosslinked tissue.

5. The medical article of claim 1 wherein said tissue comprises a deposit of at least about 0.01 mg of elemental metal per gram of tissue.

6. The medical article of claim 1 wherein said elemental metal is selected from the group consisting of zinc, gallium, lanthanum and beryllium.

7. The medical article of claim 1 wherein said tissue comprises uncrosslinked tissue.

8. The medical article of claim 1 wherein said tissue is crosslinked with glutaraldehyde.

9. The medical article of claim 1 wherein said tissue comprises a deposit of about 0.1 mg to about 20 mg of elemental metal per gram of tissue.

10. The medical article of claim 1 wherein said tissue is porcine tissue or bovine tissue.

11. The medical article of claim 1 wherein calcification of said medical article is reduced at least about 30 percent following about one month of implantation within a patient, said reduction being determined in comparison with a comparable medical article lacking said elemental metal.

12. The medical article of claim 1 wherein calcification of said medical article is reduced at least about 75 percent following about one month of implantation within a patient, said reduction being determined in comparison with a comparable medical article lacking said elemental metal.

13. The medical article of claim 1 wherein said tissue further comprises a second anticalcific elemental metal.

14. The medical article of claim 1 wherein said tissue further comprises an anticalcific metal compound.

15. A heart valve prosthesis comprising leaflets, said leaflets comprising a synthetic polymer and a deposit of anticalcific, elemental metal.

16. The heart valve prosthesis of claim 15 wherein said elemental metal is selected from the group consisting of aluminum, iron, magnesium and combinations thereof.

17. The heart valve prosthesis of claim 15 wherein said polymer is selected from the group consisting of polyamides, polyesters, polystyrenes, polyacrylates, vinyl polymers, polycarbonates, polyurethanes, poly dimethyl siloxanes, cellulose acetates, poly methyl methacrylates, ethylene vinyl acetates, polysulfones, nitrocelluloses and similar copolymers.

18. The heart valve prosthesis of claim 15 wherein calcification of said prosthesis is reduced at least about 75 percent following about one month of implantation within a patient, said reduction being determined in comparison with a comparable prosthesis lacking said elemental metal.

19. The heart valve prosthesis of claim 15 wherein said polymer comprises a deposit of about 0.1 mg to about 20 mg of elemental metal per gram of polymer.

20. The heart valve prosthesis of claim 15 wherein said polymer further comprises an anticalcific metal compound.

* * * * *